United States Patent [19]

Gray et al.

[11] Patent Number: 4,762,548

[45] Date of Patent: Aug. 9, 1988

[54] HERBICIDE COMPOSITIONS OF EXTENDED SOIL LIFE

[75] Inventors: Reed A. Gray, Saratoga; Ferenc M. Pallos, Walnut Creek, both of Calif.

[73] Assignee: Stauffer Chemical Co., Westport, Conn.

[21] Appl. No.: 764,290

[22] Filed: Aug. 12, 1985

[51] Int. Cl.$^4$ .................. A01N 25/22; A01N 37/00
[52] U.S. Cl. .......................... 71/100; 71/88; 71/118; 564/209; 564/212; 564/215; 564/219; 564/224; 564/192; 564/183; 564/185; 564/186; 564/187; 564/182; 564/199; 564/200; 562/450; 562/503; 562/505; 562/506; 562/507; 562/567; 562/574
[58] Field of Search .............. 564/209, 212; 71/100, 71/118, 87, 86

[56] References Cited

U.S. PATENT DOCUMENTS 2,864,683 12/1958 Hamm et al. .................... 71/118
4,021,224 5/1977 Rollos et al. .................... 564/209

FOREIGN PATENT DOCUMENTS 1168056 5/4984 Canada ........................... 71/118

OTHER PUBLICATIONS

Hamm et al. I, "Relation of Herbicidal activity to the Amide Moiety of N-Subst α-Chloroacetamides, J. Agric. Food Chem., 4, (1956), 518.

*Primary Examiner*—Glennon H. Hollrah
*Assistant Examiner*—Patricia L. Morris
*Attorney, Agent, or Firm*—Harry A. Pacini; Leona L. Lauder

[57] ABSTRACT

Herbicidally active thiolcarbamates are employed in combination with a certain amide extender compound, the latter in sufficient quantity to minimize soil degradation and to prolong the soil life of the former. As a result, the herbicidal effectiveness of the thiolcarbamate herbicide is significantly enhanced and prolonged, rendering a single application or multiple applications of the herbicide effective over a longer period of time. Such herbicidal compositions can optionally contain a non-phytotoxic antidotally effective amount of thiolcarbamate herbicide antidote.

3 Claims, No Drawings

HERBICIDE COMPOSITIONS OF EXTENDED SOIL LIFE

BACKGROUND OF THE INVENTION

This invention relates to herbicidal compositions and methods of use. In particular, this invention relates to herbicidal compositions comprising an herbicidally effective amount of a thiolcarbamate herbicide in combination with an extending amount of an extender compound. An extender serves to prolong the effectiveness of single or multiple applications of the thiolcarbamate herbicide in controlling undesired plant growth. The extenders of the instant invention are amides.

Thiolcarbamates are well known in the agricultural art as herbicides useful for weed control in crops such as corn, potatoes, beans, beets, spinach, tobacco, tomatoes, alfalfa, rice, peanuts, and soybeans among others. Thiolcarbamates are primarily used in preemergence application. They have been found to be particularly effective when incorporated into the soil prior to the planting of the crop. As a herbicide, the thiolcarbamate is most concentrated immediately after its application. How long thereafter the initial concentration is retained depends in large part on the particular soil used. Thus the rate at which the thiolcarbamate herbicide concentration declines following its application tends to vary from one type of soil to the next. This is evident in the observable extent of actual weed control after considerable time has elapsed.

The extender compounds of the instant invention extend the soil life of thiolcarbamate herbicides in soil which has been treated one or more times before with a thiolcarbamate herbicide or in soil which has had no previous treatment with a thiolcarbamate herbicide. Soil which has been previously treated with a thiolcarbamate herbicide is termed "pretreated soil"; whereas soil which has not been so treated is termed "non-pretreated soil."

Under certain environmental and other conditions, thiolcarbamate herbicides are degraded more rapidly in pretreated soil of certain types than in non-pretreated soil. Such pretreated soil is considered conditioned to degrade thiolcarbamates herbicides at an accelerated rate compared to non-pretreated soil.

The extenders of the instant invention prevent rapid soil degradation of thiolcarbamate herbicide. Not only do the extenders prevent the rapid soil degradation of thiolcarbamate herbicides in pretreated soil, but also prolong the herbicidally effective soil life of thiolcarbamate herbicides in non-pretreated soil.

The soil in many of the examples below showing activity of representative extenders of the instant invention has been pretreated. Such pretreatment is designed to simulate field conditions wherein a field has been repeatedly treated with a thiolcarbamate herbicide. This simulation is effected by retreating the experimental soil, employed herein within weeks of the first treatment rather than seasons later as in the fields. Such a short experimental retreatment period highly conditions the soil.

The improvement in the soil persistence of the thiolcarbamate herbicide effected by the extender compound can manifest itself in a variety of ways. Improved soil persistance can be shown by herbicidal efficacy tests, wherein the degree of weed injury is measured after a set period of time following application of the herbicide. In such a test, the extender compound is shown to increase the herbicidal effectiveness of the thiolcarbamate by increasing the persistence of the latter in the soil, and thus prolonging its effective life.

In order for a compound to qualify as an extender, it is highly desirable that the compound have no significant herbicidal activity of its own. Each of the amide extenders of the instant invention were screened for herbicidal activity, and each were shown to have no or negligible herbicidal activity.

SUMMARY OF THE INVENTION

This invention first relates to a novel group of amide compounds which have utility as extender compounds. Said compounds specifically comprise compounds having the following formula:

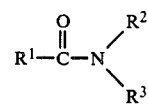

wherein $R^1$ is hydrogen, $C_1-C_6$ alkyl, $C_1-C_6$ mono-, di-, tri- or poly-haloalkyl, $C_1-C_4$ alkylthioalkyl, carboxyvinyl, carboxy-dihalovinyl, carboxyhalovinyl, $C_1-C_4$ acetoalkyl, halo-substituted phenyl, $C_1-C_4$ alkylsulfonylalkyl, or $C_1-C_4$ dihaloalkyl substituted with either unsubstituted phenyl or halo-substituted phenyl;

$R^2$ is mono- or di-haloallyl; and $R^3$ is allyl, mono- or di-haloallyl, furfuryl, $C_1-C_6$ alkoxyalkyl, allyl substituted with a $C_1-C_4$ alkyl group, $C_1-C_4$ alkyl substituted with $C_3-C_6$ cycloalkyl, benzyl or $C_2-C_6$ alkynyl mono- or di-substituted with $C_1-C_4$ alkyl.

In a first preferred embodiment of the invention, the novel compounds of the instant invention are defined such that $R^1$ is $C_1-C_4$ mono-, di-, tri- or poly-haloalkyl, $C_1-C_4$ alkylthioalkyl, carboxyvinyl, carboxy (mono- or dihalo)vinyl, cyclopropylmethyl or $C_1-C_4$ alkylsulfonylalkyl;

$R^2$ is monohaloallyl; and $R^3$ is furfuryl, $C_1-C_6$ alkoxyalkyl, allyl, 2-methylallyl, benzyl or monohaloallyl.

In a second preferred embodiment of the invention, the novel compounds of the instant invention are such that $R^1$ is $C_1-C_4$ mono-, di- or trihaloalkyl, methylthiomethyl, carboxyvinyl, carboxychlorovinyl, carboxydichlorovinyl or methylsulfonylmethyl;

$R^2$ is monochloroallyl; and $R^3$ is furfuryl, benzyl, methoxyethyl, 2-methylallyl, allyl or monochloroallyl.

In a third preferred embodiment of the invention, the novel compounds of the instant invention are defined such that $R^1$ is 1,1-dichloroethyl, chloromethyl, dichloromethyl, $C_1C_4$ trichloroalkyl, methylthiomethyl, $C_1-C_4$ trifluoroalkyl, $C_1-C_4$ tribromoalkyl;

$R^2$ is 3-chloroallyl; and $R^3$ is 3-chloroallyl, allyl, 2-methylallyl, benzyl, furfuryl, methoxyethyl, or cyclopropylmethyl.

In the fourth preferred embodiment, the compounds of the instant invention are defined such that $R^1$ is dichloromethyl, trichloromethyl, chloromethyl, 1,1-dichloroethyl, tribromomethyl, trifluoromethyl or methylthiomethyl;

$R^2$ is 3-chloroallyl; and $R^3$ is 3-chloroallyl, 2-methylallyl, allyl, methoxyethyl, furfuryl, benzyl, or cyclopropylmethyl.

A preferred $R^2$ and $R^3$ group of the instant compounds is 3-chloroallyl. It is preferred that that moiety be in the trans configuration.

Exemplary compounds of the instant invention are as follows: N-methoxyethyl-N-(3-chloroallyl) trichloroacetamide; N-furfuryl-N-(3-chloroallyl) trichloroacetamide; N-(3-chloroallyl)-N-benzyl trichloroacetamide; N-methylcyclopropyl-N-3-chloroallyl trichloroacetamide; N,N-bis-(3-chloroallyl)-2,2-dichloropropionamide; N,N-bis-(3-chloroallyl) chloroacetamide; N,N-bis-(3-chloroallyl) dichloroacetamide; N,N-bis-(3-chloroallyl) trichloroacetamide; N-(2-methyl)-allyl-N-(3-chloroallyl) trichloroacetamide; N,N-bis-(3-chloroallyl) methylthioacetamide; N,N-bis-(3-chloroallyl) tribromoacetamide; N,N-bis-(3-chloroallyl) trifluoroacetamide; or N-allyl-N-3-chloroallyl dichloroacetamide.

This invention further comprises a novel herbicidal composition of extended soil life, comprising an herbicidally effective amount of a thiolcarbamate herbicide and an extending amount of an amide extender compound. In a preferred embodiment, the compositions of this invention include a substantially nonphytotoxic, antidotally effective amount of a thiolcarbamate herbicide antidote.

Such prolongation of the thiolcarbamate herbicide's activity is effected by the extender in both pretreated and non-pretreated soil.

This invention further relates to a method of extending the soil life of a thiolcarbamate herbicide comprising applying to the soil containing said thiolcarbamate herbicide or to which said thiolcarbamate herbicide is to be applied an extending amount of a certain amide extender compound sufficient to extend the soil life of said thiolcarbamate herbicide.

This invention further relates to a method of controlling undesirable vegetation comprising applying to the locus where control is desired both an herbicidally effective amount of a thiolcarbamate herbicide and an extending amount of a certain amide extender compound sufficient to extend the soil life of said thiolcarbamate herbicide.

Further, this invention relates to a method of minimizing the soil degradation of thiolcarbamate herbicides.

In particular, this invention relates to a novel herbicidal composition comprising (a) an herbicidally effective amount of a thiolcarbamate having the formula $$R^4-S-\overset{O}{\underset{\|}{C}}-N\overset{R^5}{\underset{R^6}{\diagdown}}$$

wherein $R^4$ is $C_1-C_6$ alkyl; phenyl; $C_7-C_9$ phenylalkyl; $C_3-C_6$ alkenyl; $C_3-C_6$ haloalkenyl; or $C_7-C_9$ phenylakyl, mono- or poly-substituted on the phenyl ring with halogen;

$R^5$ and $R^6$ are either selected independently from $C_1-C_6$ alkyl or $C_5-C_7$ cycloalkyl or combined to form conjointly $C_4-C_8$ alkylene; and (b) an extending amount of a compound having the formula $$R^1-\overset{O}{\underset{\|}{C}}-N\overset{R^2}{\underset{R^3}{\diagdown}}$$

wherein $R^1$ is hydrogen, $C_1-C_6$ alkyl, $C_1-C_6$ mono-, di-, tri- or poly-haloalkyl, $C_1-C_4$ alkylthioalkyl, carboxyvinyl, carboxy-dihalovinyl, carboxyhalovinyl, $C_1-C_4$ acetoalkyl, halo-substituted phenyl, $C_1-C_4$ alkylsulfonylalkyl, $C_1-C_4$ dihaloalkyl substituted with either unsubstituted phenyl or halo-substituted phenyl;

$R^2$ is of mono- or di-haloallyl; and $R^3$ is allyl, mono- or di-haloallyl, furfuryl, $C_1-C_6$ alkoxyalkyl, allyl substituted with a $C_1-C_4$ alkyl group, $C_1-C_4$ alkyl substituted with $C_3-C_6$ cycloalkyl, benzyl or $C_2-C_6$ alkynyl mono- or di-substituted with $C_1-C_4$ alkyl.

In a first preferred embodiment of the invention, the thiolcarbamate herbicides shown above are defined such that $R^4$ is $C_1-C_6$ alkyl, allyl or haloallyl;

$R^5$ is $C_1-C_6$ alkyl; and $R^6$ is $C_1-C_6$ alkyl or $C_5-C_7$ cycloalkyl.

In a second preferred embodiment of the invention, thiolcarbamate herbicides are defined such that $R^4$ and $R^5$ are each independently $C_1-C_6$ alkyl; and $R^6$ is $C_1-C_6$ alkyl or cyclohexyl.

In a third preferred embodiment of the invention, thiolcarbamate herbicides are defined such that $R^4$ and $R^5$ are each independently $C_1-C_4$ alkyl; and $R^6$ is either $C_1-C_4$ alkyl or cyclohexyl.

In a fourth preferred embodiment, thiolcarbamate herbicides are defined such that $R^4$ is n-propyl or ethyl;

$R^5$ is n-propyl, n-butyl, isobutyl or ethyl; and $R^6$ is n-propyl, isobutyl, cyclohexyl or ethyl.

Exemplary thiolcarbamate herbicides of the invention include S-ethyl N,N-di-n-propyl thiolcarbamate (EPTAM®); S-ethyl hexahydro-azepine-1-carbothioate (ORDRAM®): S-ethyl N,N-diisobutyl thiolcarbamate (SUTAN®); S-n-propyl N,N-di-n-propyl thiolcarbamate (VERNAM®); S-ethyl N-ethyl-N-cyclohexyl thiolcarbamate (RO-NEET®); S-n-propyl-N-n-butyl-N-ethyl thiolcarbamate (TILLAM®); S-(2,3-dichloroallyl) N,N-diisopropyl thiolcarbamate (diallate); S-(2,3,3-trichloroallyl) N,N-diisopropyl thiolcarbamate (triallate); or S-(4-chlorophenyl) methyl N,N-diethyl thiolcarbamate (thiobencarb).

Preferred extenders of the instant invention are those amides as defined above wherein $R^1$ is $C_1-C_4$ mono-, di- or tri-haloalkyl or $C_1-C_2$ alkylthioalkyl;

$R^2$ is monohaloallyl; and $R^3$ is benzyl; cyclopropylmethyl; monohaloallyl, allyl, allyl substituted with ethyl or methyl; furfuryl, or $C_1-C_4$ alkoxyalkyl.

Further preferred extenders of the instant invention are those amides as defined above wherein $R^1$ is tribromomethyl, trichloromethyl, trifluoromethyl, dichloromethyl, chloromethyl, 1,1-dichloroethyl, or methylthiomethyl;

$R^2$ is monochloroallyl; and

R³ is benzyl, cyclopropylmethyl, monochloroallyl, allyl, 2-methylallyl, furfuryl, or methoxyethyl.

Even further preferred extenders of the invention are those wherein

R¹ is as defined immediately above;
R² is 3-chloroallyl;
R³ is defined as immediately above except that monochloroallyl is more narrowly construed as 3-chloroallyl.

Still even preferred extenders of the invention are those wherein

R¹ is as defined immediately above;
R² is 3-chloroallyl; and
R³ is 3-chloroallyl, furfuryl, cyclopropylmethyl, 2-methylallyl or methoxyethyl.

Even more preferred extenders of the invention are those wherein

R¹ is trifluoromethyl, 1,1-dichloroethyl or trichloromethyl;
R² is 3-chloroallyl; and
R³ is 3-chloroallyl, methoxyethyl, furfuryl, cyclopropylmethyl or 2-methylallyl.

A still preferred embodiment of the invention is that wherein the extenders are defined such that R¹ is trichloromethyl, trifluoromethyl or 1,1-dichloroethyl;
R² is 3-chloroallyl; and
R³ is 3-chloroallyl, methoxyethyl, 2-methylallyl or cyclopropylethyl.

Still further preferred embodiments of the invention include extenders wherein

R¹ is trichloromethyl;
R² is 3-chloroallyl; and
R³ is 2-methylallyl or 3-chloroallyl.

Exemplary extenders of the instant invention are N-(2-methyl)allyl-N-(3-chloroallyl) trichloroacetamide; N,N-bis-(3-chloroallyl) trichloroacetamide; N-(3-chloroallyl)-N-cyclopropylmethyl trichloroacetamide; N,N-bis-(3-chloroallyl) 2,2-dichloroacetamide; and N-methoxyethyl N-(3-chloroallyl) trichloroacetamide.

The term "alkyl" is used herein in its normal meaning and is intended to include both straight-chain and branched-chain groups.

The terms "alkyl," "alkoxy," "alkylthio," and "alkynyl" are intended to include both straight-chain and branched-chain groups, such as methyl, ethyl, n-propyl, isopropyl, n-butyl, sec-butyl, tert-butyl, methoxy, ethoxy, isopropoxy, tert-butoxy, methylthio, ethylthio, n-butylthio, 1,1-dimethylpropynyl, ethynyl, 1,2-diethylpropynyl, 2-butynyl, etc. All carbon atom ranges in this specification and the appended claims are intended to be inclusive of their upper and lower limits.

"Haloalkyl" as used herein refers to alkyl compounds that are substituted, meaning mono- or poly-substituted, with halogen. Polysubstituted with halogen refers to compounds substituted with one or more halogen atoms, as, for example, trichloromethyl, 1,1-dichloroethyl, dichloromethyl or 1,2-dibromomethyl moieties.

The term "halogen atom" or "halo" is used to designate fluorine, chlorine, bromine, or iodine atoms, as well as any combination thereof.

The term "herbicide," as used herein, means a compound which adversely controls or modifies the growth of plants. By the term "herbicidally effective amount" is meant an amount of compound which causes an adverse modifying effect upon the growth of plants. By "plants" is meant germinant seeds, emerging seedlings and established vegetation, including roots and above-ground portions. Such adverse controlling and modifying effects include all deviations from natural development, for example, killing, retardation, defoliation, desiccation, regulation, stunting, tillering, stimulation, leaf burn, dwarfing and the like.

The phrase "to extend the soil life of said thiolcarbamate" is used herein to denote the effect whereby herbicidal effectiveness of the thiolcarbamate is maintained over time. An extended soil life can be manifest in a slower rate of decline of weed killing potency.

An "extending amount" means an amount of an extender compound which is sufficient to prolong the soil life of a thiolcarbamate herbicide significantly.

DETAILED DESCRIPTION OF THE INVENTION

Many of the thiolcarbamate herbicides within the scope of the present invention can be prepared by the process described in U.S. Pat. No. 2,913,327 (Tilles et al., Nov. 17, 1959).

Other of the thiolcarbamate herbicides within the scope of this invention can be prepared by methods described in U.S. Pat. Nos. 3,582,314; 3,330,821 and 3,330,643.

The amide extenders within the scope of the present invention can be prepared by the following general method. An appropriately substituted amine is reacted with an acid chloride such as trichloroacetyl chloride in an inert solvent such as methylene chloride in the presence of an acid acceptor such as triethylamine. The following examples detail and are representative of this method, and further provide variants of the general method.

EXAMPLE 1

N,N-bis-(3-chloro)allyl chloroacetamide

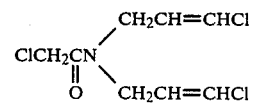

N,N-bis-(3-chloro)allyl amine [4.15 grams (g), 0.025 mol] and 2.55 g (0.025 mol) triethylamine were stirred in 70 milliliters (70) dichloromethane. The reaction mixture was cooled to approximately 5°–10° C. with an ice-water bath. Chloroacetyl chloride (2.84 g, 0.025 mol) was added dropwise to the mixture. Upon completion of the addition, the mixture was stirred at room temperature for 4 hours. The reaction mixture was then washed with water and dried with sodium sulfate. Rotary evaporation yielded a total of 5.7 g of the above-named product.

The structure was confirmed by infrared spectroscopy (IR), nuclear magnetic resonance (NMR) and mass spectroscopy (MS).

EXAMPLE 2

N,N-bis-(3-chloroallyl methylthioacetamide)

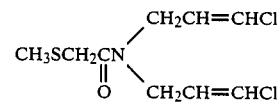

N,N-bis-(3-chloro)allyl chloroacetamide (5.7 g, 0.024 mol) (the product of Example 1) was dissolved in 20 ml tetrahydrofuran. The resulting solution was then added dropwise to 1.7 g (0.024 mol) sodium methyl mercaptide in 50 ml tetrahydrofuran. The mixture was stirred at room temperature overnight. The mixture was then decanted, and the liquid layer saved. The solid slurry was washed with acetone and filtered. The liquids were combined and dried with sodium sulfate. Rotary evaporation yielded 5.25 g of the above-named product.

The structure was confirmed by IR, NMR and MS.

EXAMPLE 3

N-(3-chloro)allyl-N-methoxyethyl trichloroacetamide

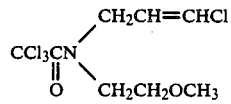

N-(3-chloro)allyl-N-methoxyethylamine (2.25 g, 0.015 mol) and 1.52 g (0.015 mol) triethylamine were stirred in 70 ml dichloromethane. The reaction was kept at approximately 5° C. with an ice-water bath. Trichloroacetyl chloride (2.73 g, 0.015 mol) in 10 ml dichloromethane was added dropwise to the cooled solution. Upon completion of the addition, the mixture was stirred at room temperature for 6 hours. The reaction mixture was then washed twice with saturated brine and dried with sodium sulfate. Rotary evaporation yielded 4.1 g of the above-named product.

The structure was confirmed by NMR, IR and MS.

EXAMPLE 4

N,N-bis-(3-chloroallyl) formamide

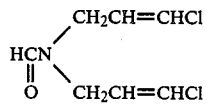

Bis-(3-chloroallyl)amine (2.5 g, 0.015 mol) and 25 ml formic acid were combined and refluxed for 5 hours. The mixture was stripped under a vacuum from a hot-water bath. The yield was 2.6 g of the above-named product.

The structure was confirmed by IR, NMR and MS.

EXAMPLE 5

N,N-bis-(3-chloroallyl) dichloromaleic monoamide

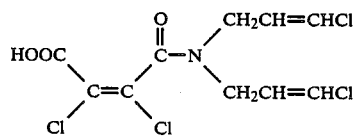

Dichloromaleic anhydride (1.7 g, 0.01 mol) and 30 ml methylene chloride were stirred under a mild reflux. Bis-(3-chloroallyl)amine (1.7 g, 0.01 mol) was then added. The exothermic reaction yielded a clear solution. The solution was stirred at room temperature for 3 hours. The mixture was stripped, resulting in 3.3 g of the above-named product.

The structure was confirmed by NMR and MS.

Representative extender compounds of this invention which can be prepared by the methods exemplified above or by analogous methods are listed in Table I, infra.

The objects of the present invention are achieved by applying an amide extender compound to the soil at an agricultural field site in conjunction with the thiolcarbamate herbicide. The two compounds can be applied simultaneously in a single mixture or in separate formulations, or they can be applied in succession, with either one following the other. In successive application, it is preferable to add the compounds as close in time as possible.

The herbicide extending effect is operable over a wide range of weight ratios of the two compounds. It is most convenient, however, to apply the compounds at a weight ratio of about 0.2:1 to about 30:1 (herbicide/extender), preferably about 0.5:1 to about 20:1, and most preferably about 0.5:1 to about 12:1.

Thiolcarbamate herbicides whose soil life is sought to be extended in the present invention include those disclosed in U.S. Pat. Nos. 2,913,327; 3,582,314; 3,330,821; and 3,330,643, and preferably include S-ethyl N,N-di-n-propylthiolcarbamate; S-ethyl N,N-diisobutylthiolcarbamate; S-n-propyl N,N-di-n-propylthiolcarbamate; S-n-propyl ethyl-n-butylthiolcarbamate; S-ethyl-N-ethyl-N-cyclohexylthiolcarbamate; S-ethyl hexahydro-1H-azepine-1-carbothioate; S-benzyl N,N-di-n-propylthiolcarbamate; S-(4-chlorobenzyl)-N,N-diethyl thiolcarbamate; S-benzyl N-ethyl-N-1,2-dimethylpropylthiolcarbamate; S-benzyl-N,N-di-sec-butyl thiolcarbamate; S-(2,2,3-trichloroallyl)-N,N-di-isopropyl thiolcarbamate; and S-(2,3-dichloroallyl)-N,N-diisopropyl thiolcarbamate.

THIOLCARBAMATE HERBICIDE ANTIDOTES

A wide range of chemical substances have been found to be effective as thiolcarbamate herbicide antidotes, and the preferred compositions of this invention may include any one or more of such antidotes. The variety of crops on which the present composition is useful can be significantly broadened by the use of an antidote to protect one crop from injury and render the composition more selective against weeds. Some of the more important types of antidotes are amides of haloalkanoic acids, aromatic oxime derivatives, thiazole carboxylic acids and derivatives, and 1,8-naphthalic anhydride.

Amides of haloalkanoic acids have the generalized formula

in which R is a mono- or poly-haloalkyl group. The halogens may be variously chloro, bromo or iodo; chloro is the preferred halogen, and the preferred group for R in these compounds in general is dichloromethyl, $Cl_2CH-$, i.e., the compounds are amides of dichloroacetic acid. In such compounds the nitrogen is further substituted by at least one other functional group. This class of compounds also includes those in which the nitrogen forms a portion of a heterocyclic ring with substituents, as will be described below.

Antidotes of this type are described in a number of publications such as U.S. Pat. Nos. 4,021,224; 4,256,481; and 4,294,764, and British Pat. No. 1,521,540. U.S. Pat.

No. 4,021,224 contains a broad disclosure of such types of compounds and indicates a great many possibilities for mono- or di-substitution on the nitrogen atom.

One type of antidote disclosed in U.S. Pat. No. 4,021,224 is N,N-diallyl dichloroacetamide,

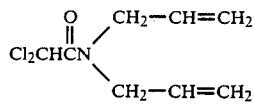

which is included as an antidote in several commercial products containing thiolcarbamate herbicides. This antidote differs from the amide extender of the present invention in that one of the allyl moieties of the amide extenders is always halogenated.

Another class of haloalkanoic acid amides is that in which the nitrogen atom is contained in an oxazolidine ring. Preferably R is dichloromethyl, and these oxazolidines have the general formula

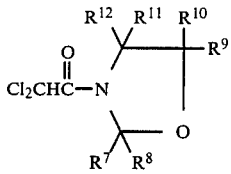

In this formula, $R^7$, $R^8$, $R^9$, $R^{10}$, $R^{11}$ and $R^{12}$ are variously independently hydrogen, lower alkyl or phenyl, or $R^7$ and $R^8$ taken together form an alkylene group, preferably a butylene, pentylene or hexylene group optionally substituted by one or two methyl groups. Compounds of these types are disclosed in a number of patents including U.S. Pat. Nos. 4,021,224 and 4,256,481. Representative compounds of this type include (where not specifically mentioned the radical is hydrogen):

2,2-dimethyl-N-dichloroacetyl oxazolidine ($R^7$ and $R^8$=methyl);

2,2,5-trimethyl-N-dichloroacetyl oxazolidine ($R^7$, $R^8$ and $R^{11}$=methyl);

2,2-dimethyl-5-n-propyl-N-dichloroacetyl oxazolidine ($R^7$, $R^8$=methyl, $R^{11}$=n-propyl);

2,2-dimethyl-5-phenyl-N-dichloroacetyl oxazolidine ($R^7$, $R^8$=methyl, $R^{11}$=phenyl);

2,2-spirocyclohexyl-N-dichloroacetyl oxazolidine ($R^7$ plus $R^8$ taken together=pentamethylene).

Other compounds in which $R^7$ and $R^8$ taken together are alkylene are disclosed for instance in British Pat. Nos. 1,512,540 and 2,023,582 and Hungarian Pat. No. 181,621.

A third type of haloalkanoic acid amide is disclosed generally in U.S. Pat. No. 4,294,764 and has the general formula

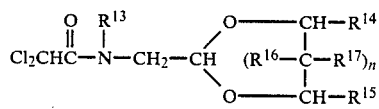

in which $R^{13}$ may be one of a number of alkyl, alkenyl or alkynyl moieties; $R^{14}$, $R^{15}$, $R^{16}$ and $R^{17}$ are independently hydrogen or methyl; and n is 0 or 1. A representative compound of this type is the compound N-(1,3-dioxolan-2-yl-methyl)-N-(2-propenyl)-2,2-dichloroacetamide, which has the formula

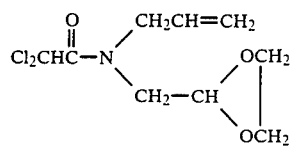

This corresponds to the previous formula in which $R^{13}$ is 2-propenyl, $R^{14}$ and $R^{15}$ are both hydrogen and n is 0.

Oxime derivatives which are suitable for use as antidotes with thiolcarbamate herbicides are disclosed, for instance in U.S. Pat. Nos. 4,070,389 and 4,269,775 and have the general formula

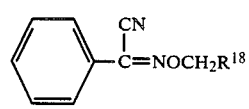

in which $R^{18}$ is cyano or a number of other moieties as indicated in U.S. Pat. No. 4,269,775. Representative compounds of this type are those in which $R^{18}$ is cyano and in which $R^{18}$ is 1,3-dioxolan-2-yl. The latter compound has the chemical name O-[2-(1,3-dioxolanyl)methyl]-alphacyanobenzaldoxime.

Thiazole carboxylic acids and derivatives suitable for use as thiolcarbamate antidotes are disclosed generally in U.S. Pat. No. 4,199,506 and have the general formula

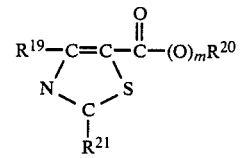

in which $R^{19}$ is alkyl, haloalkyl or trialkoxymethyl; $R^{20}$ is variously hydrogen, agriculturally acceptable cations or various hydrocarbamyl or substituted hydrocarbamyl moieties; and $R^{21}$ is chloro, bromo, iodo, lower alkoxy or substituted or unsubstituted phenoxy. A representative member of this class is the compound benzyl-2-chloro-4-trifluoromethyl-5-thiazole carboxylate ($R^{19}$=trifluoromethyl; $R^{20}$=benzyl; $R^{21}$=chloro; m=1).

Another useful thiolcarbamate herbicide antidote compound is disclosed in European Pat. No. 0104495 as having the formula

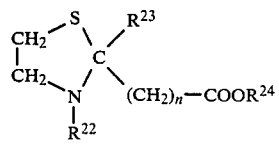

wherein $R^{22}$ represents the group

in which $R^{25}$ represents a $C_1$-$C_3$ haloalkyl containing from 1 to 3 halogen atoms or a phenyl group optionally substituted;

$R^{23}$ represents a hydrogen atom, a methyl or a phenyl;

$R^{24}$ represents a $C_1$-$C_8$ alkyl group, a $C_5$-$C_6$ cycloalkyl group, a cyclohexylmethyl group, a phenyl group optionally substituted, a benzyl group optionally substituted, an allyl or propargyl group; and n is zero or one.

A representative antidote of that group would be:

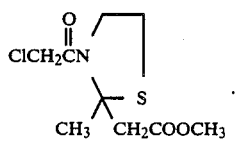

The amount of a given antidote to be utilized in combination with the thiolcarbamate herbicide/extender composition of this invention and the manner of its utilization will vary according to the particular antidote to be employed, the crop which is to be protected, the amount or rate of herbicide to be applied, and the soil and climatic conditions of the agricultural environment in which the mixture is to be applied. The selection of a specific antidote for use in the thiolcarbamate herbicide/extender composition, the manner in which it is to be applied (e.g., tank mix, in-furrow application, seed treatment, etc.), the determination of activity which is nonphytotoxic but antidotally effective, and the amount necessary to provide this result, can be readily performed utilizing the test procedures in the cited patents such as U.S. Pat. No. 4,021,224 in accordance with common practice in the art.

For other descriptions of antidotes and methods of their use, reference is made to U.S. Pat. No. 3,959,304, issued to Teach on May 25, 1976; U.S. Pat. No. 3,989,503, issued to Pallos et al. on Nov. 2, 1976; U.S. Pat. No. 3,131,509, issued to Hoffman on May 5, 1964; U.S. Pat. No. 3,564,768, issued to Hoffman on Feb. 3, 1971; U.S. Pat. No. 4,137,070, issued to Pallos et al. on Jan. 30, 1979; U.S. Pat. No. 4,294,764, issued to Rinehart on Oct. 13, 1981; U.S. Pat. No. 4,256,481, issued to Gardi et al. on May 17, 1981; U.S. Pat. No. 4,415,353, issued to Pallos et al. on Nov. 15, 1983; and U.S. Pat. No. 4,415,352, issued to Pallos et al. on Nov. 15, 1983. A still further useful antidote is 1,8-naphthalic anhydride.

The antidote is applied in conjunction with a thiolcarbamate herbicide and an amide extender of this invention in a non-phytotoxic antidotally effective amount. By "non-phytotoxic" is meant an amount of the antidote which causes at most minor injury to the desired crop species. By "antidotally effective" is meant an amount of the antidote which substantially decreases the extent of injury caused by the thiolcarbamate herbicide to the desired crop species. The preferred weight ratio of herbicide to antidote is from about 0.1:1 to about 40:1. Another preferred weight ratio range is from about 3:1 to about 25:1. An even more preferred weight ratio range is from about 5:1 to about 20:1.

The following examples are offered to illustrate the compositions, methods, and effectiveness of the present invention, and are not intended to limit the invention in any way.

EXTENDER ACTIVITY EXAMPLES

Herbicidal Activity Improvement Tests

Table 1 below offers herbicidal activity test data for representative extender compounds within the scope of this invention showing their effectiveness in prolonging the herbidical activity of thiolcarbamate herbicides. The effect is observed by comparing the extent of weed control in test flats treated with a thiolcarbamate herbicide against that occurring in similar flats treated with both the thiolcarbamate herbicide and an amide extender compound. The soil used in such tests was a sandy loam soil from Sunol, Calif., which was pre-treated with the thiolcarbamate herbicide to simulate a typical field which had received previous herbicide applications.

In most instances, the tests were run with a thiolcarbmate and antidote formulation (see procedure IIa and IIb below), except for those test results marked with a single asterisk indicating that the soil was pre-treated and then treated with a thiolcarbamate herbicide alone. (See Procedure 1A and 1B below).

The effectiveness of the extender in minimizing the degradation of the thiolcarbamate herbicide in the soil is then verified by comparing the herbicidal activity of the extender alone when pre-plant incorporated at 4 lb/acre and where indicated at lower rates, 0.05, 1.0 and 2.0 lb/acre. The herbicide alone or the herbicide and antidote without extender showed negligible herbicidal activity in conditioned soil, that is between 0-5%. The extender compounds in each instance greatly increased the herbicidal activity in conditioned soil.

The last column of Table 1 indicates the nonexistent or negligible herbicidal activity of each extender in non-treated soil at 4 lb/acre. In most instances, the amide extender was pre-plant incorporated, except where PRE is noted after the test result, indicating that the extender was pre-emergent surface applied at 4 lb/acre. (See Procedure 3A and 3B below.)

The procedures below detail the methods used to achieve the results tabulated in Table 1.

1: Tests with S-ethyl N,N-di-n-propyl Thiolcarbamate and No Antidote

A. Soil Pre-Treatment

A solution was prepared by diluting an emulsifiable liquid concentrate containing 6 lb/gal (0.72 kg/l) (76.8% by weight) of the herbicide S-ethyl N,N-di-n-propylthiolcarbamate in 200 ml of water, such that the resulting concentration of herbicide in the solution was 2000 mg/l. Two hundred ml of this solution was then added to 200 lb (90.8 kg) of soil to which 17—17—17 fertilizer (N—$P_2O_5$—$K_2O$ on a weight basis) had been previously added to a concentration of 50 ppm by weight with respect to the soil. The mixture was mixed in a rotary mixer for 10 to 30 minutes.

The soil was then placed in round plastic containers, 7.5 inches (19.0 cm) in diameter by 7.5 inches (19.0 cm) deep. The herbicidal rate applied was equivalent to 3 lb/acre. The soil was tamped and leveled with a row marker to impress one row across the width of each container. This row was seeded with watergrass (*Echinochloa crus-galli*). Sufficient seeds were planted to produce several seedlings. The containers were then placed in a greenhouse maintained at 20° C. to 30° C. and watered daily by sprinkler.

About six weeks after treatment, the soil was allowed to dry out and the plant foliage was removed. The soil was then passed through a 0.25 inch (0.64 cm) screen to remove plant roots and clods.

B. Herbicide Test

A solution was prepared by diluting an emulsifiable liquid concentrate containing 6 lb/gal (0.72 kg/l) (76.8% by weight) of the herbicide S-ethyl N,N-di-n-propylthiolcarbamate in 675 ml of water such that the resulting concentration of herbicide in the solution was 1.14 mg/ml. Five ml of this solution when added to three pounds of soil yielded a quantity in the soil equivalent to three pounds of herbicide per acre.

The extender compounds were used in technical form. Each representative extender was dissolved in 5 ml acetone and 14.5 ml water such that the resulting concentration of the extender in the solution was 1.54 mg/ml. Five ml of this solution when added to three pounds of soil yielded a quantity in the soil equivalent to four pounds of extender per acre.

Five ml of the extender solution and 5 ml of the herbicide solution were tank-mixed. The resultant mixture of 10 ml was then added to 3 lbs of soil and incorporated into the soil by a rotary mixer. Thus, 10 ml of the mixture and 3 pounds of soil were placed in rotary mixer and incorporated, yielding a quantity of herbicide and extender in the soil of 3 and 4 lb/A, respectively.

Some of the extenders, as noted in the table, were tested at varying rates. In those cases, the appropriate ml of the extender solution were tank-mixed with 5 ml of the herbicide stock solution to yield the desired application rates of 0.5, 1.0 or 2.0 lb/acre.

The treated soil was then placed in aluminum flats which were approximately 3.5 inches deep, 7.5 inches wide, and 2.5 inches long (8.9×19.5×6.4 cm). The soil was tamped and leveled with a row marker to impress six rows across the width of the flat. The test weeds were as follows:

| COMMON NAME | ABBREVIATION | SCIENTIFIC NAME |
|---|---|---|
| watergrass | WG | Echinochloa crus-galli (L.) |
| wild oats | WO | Avena fatua (L.) |
| shattercane | SHC | Sorghum bicolor (L.) Moench |

R-10 milo (Sorghum bicolor) was also used as a plant growth indicator. Two rows of watergrass were planted.

One row of DeKalb XL-25A corn of species Zea mays (L.) was also planted.

Sufficient seeds were planted to produce approximately 20-25 seedlings per row. The flats were then placed in a greenhouse maintained at 70° to 85° F. (21° to 30° C.) and watered daily by sprinkler.

Approximately three weeks after treatment, the degree of weed control was estimated and recorded as a percentage compared to the growth of the same species in a check flat of the same age which had been seeded in conditioned soil but not treated with either an herbicide or an extender The rating scale ranges from 0 to 100%, where 0 equals no effect with plant growth equal to the untreated check, and 100 equals complete kill.

2: Tests with S-ethyl N,N-di-n-propyl thiolcarbamate and the Antidote N,N-diallyl Dichloroacetamide These procedures are essentially the same as that of 1A and 1B except that the antidote N,N-diallyl dichloroacetamide was applied with the herbicide.

The stock solutions described in 1(B) were formulated, and additionally a stock solution containing a thiolcarbamate herbicide and an antidote was prepared as follows:

An emulsifiable liquid concentrate of S-ethyl-N,N-di-n-propylthiolcarbamate (82.8%) and of N,N-diallyl-dichloroacetamide (6.9%) was diluted in water such that the resulting concentration of thiolcarbamate herbicide in the solution was 1.14 mg/ml. The weight ratio of the thiolcarbamate herbicide to antidote was 12:1.

An appropriate amount of the stock solution of each representative extender was applied to yield the desired application rate. The rest of the procedure of 1(B) including the evaluation criteria was followed.

Table 1 indicates where unasterisked the test results wherein the thiolcarbamate herbicide and antidote were applied at 3 and 0.25 lb/acre, respectively, by pre-plant incorporation, and the extender was applied at 4.0, 2.0, 1.0 or 0.5 lb/acre by pre-plant incorporation as described above in 1.

3: Herbicidal Screening Tests for Extender Alone

The last column of Table 1 as noted above shows herbicidal screening data for the representative extender compounds when tested alone at 4 lb/acre. In most cases, the extenders were pre-plant incorporated except wherein an asterisk indicates that they were pre-emergent surface applied.

(3A) Pre-Plant Incorporation Test:

The soil used in these tests was sandy loam soil from Sunol, Calif. to which 17—17—17 fertilizer (N—P-$_2$O$_5$—K$_2$ on a weight basis) had been added to a concentration of 50 ppm by weight with respect to the soil.

The extender compounds were used in technical form. These materials were added to 5 ml acetone and 14.5 ml water such that the resulting concentration of the extender in the solution was 1.54 mg/ml. Five or ten ml of this solution was added to three pounds of soil in a rotary mixer, and mixed thoroughly, yielding a quantity of extender in the soil equivalent to 4 lb/acre.

The treated soil was then placed in aluminum flats which were approximately 2.5 inchs deep, 3.5 inches wide, and 7.5 inches long (6.4 cm×8.9 cm×19.0 cm). The soil was tamped and leveled with a row marker to impress six rows across the width of the flat. The test weeds were as follows:

| COMMON NAME | ABBREVIATION | SCIENTIFIC NAME |
|---|---|---|
| watergrass | WG | Echinochloa crus-galli |
| wild oats | WO | Avena fauta |
| shattercane | SH | Sorghum bicolor |

Further, R-10 milo (Sorghum bicolor) was also planted as a plant growth indicator, and X-10 corn (Zea maize) was planted as a crop sensitivity indicator. Two rows of watergrass were planted. One row of each of the other weeds, plant growth indicator and crop were planted.

Sufficient seeds were planted to produce several seedlings per inch in each row. The flats were then placed in a greenhouse maintaineed at 70° to 85° F. (21° to 30° C.) and watered daily by sprinkler. Two weeks after treatment, the degree of injury or control is determined by comparison with untreated check plants of the same age. The injury rating from 0 to 100% is recorded for each species as percent control with 0% representing no injury and 100% representing complete kill.

3(B) Pre-emergence herbicide test.

On the day preceding treatment, seeds of eight different weed species are planted in loamy sand soil in individual rows using one species per row across the width of a flat. The seeds used are green foxtail (FT) (*Setaria viridis*), watergrass (WG) (*Echinochloa crus-galli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), redroot pigweed (PW) (*Amaranthus retroflexus*) or curly dock (CD) (*Rumex crispus*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the extender compound to be tested were weighed out on a piece of glassine weighing paper. The paper and compound are placed in a 60 (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results tabulated in Table 1 indicate that each of the extender compounds significantly increased the herbicidal activity of the herbicide alone or herbicide and antidote formulations in conditioned soil. These results were unexpected in that as shown in the last column, none of the extenders had any significant herbicidal activity of their own.

TABLE 1

HERBICIDAL ACTIVITY AND EXTENDING ACTIVITY OF EXTENDERS

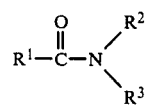

c = Average of 2 tests.
e = Average of 5 tests.
y = Herbicidal Activity at 4 lb/Acre PPI unless otherwise indicated.
Herbicide: S—ethyl N,N—di-n-propyl thiolcarbamate containing the antidote N,N—diallyl dichloroacetamide in a 12:1 weight ratio
*Indicates EPTAM: S—ethyl N,N—di-n-propyl thiocarbamate without the antidote was applied.
Herbicide Application Rate: 3 lb/Acre
Evaluation Time: Three weeks after treatment.
Soil: Pre-treated (conditioned) for extending activity tests
Non-treated (non-conditioned) for herbicidal screening of extenders alone.
PRE: Pre-emergent surface application
PPI: Pre-plant incorporation
Without Extender (Herbicide and Antidote or Herbicide Alone in Conditioned Soil): Herbicidal activity is approximately 0% weed control (between 0–5%)

| Cmpd. No. | $R^1$ | $R^2$ | $R^3$ | Eradicane + Extender * = Eptam + Extender | | | | Extender Alone |
| --- | --- | --- | --- | --- | --- | --- | --- | --- |
| | | | | 3 + 0.05 | 3 + 1 | 3 + 2 | 3 + 4 | 4 lb/AY |
| 1 | $CHCl_2$ | $CH_2CH=CHCl$ | $CH_2CH=CHCl$ | — | — | — | 92 | |
| 2 | $CH_2Cl$ | $CH_2CH=CHCl$ | $CH_2CH=CHCl$ | 22 | 40 | 67 | $88^e$ | 0 |
| | | | | — | — | — | 93 | 0 |
| 3 | $C_2H_5$ | $CH_2CH=CHCl$ | $CH_2CH=CHCl$ | 12 | 27 | 43 | 75c | |
| 4 | $CCl_3$ | $CH_2CH=CHCl$ | $CH_2CH=CHCl$ | — | — | — | 33 | 0 PRE |
| | | | | — | — | — | 92 | 0 |
| 5 | $CHCl_2$ high cis** | $CH_2CH=CHCl$ | $CH_2CH=CHCl$ | 82 | 88 | 93 | 95 | |
| | | | | 2 | 5 | 9 | 26 | 0 |
| 6 | $CHCl_2$ high trans** | $CH_2CH=CHCl$ | $CH_2CH=CHCl$ | 14 | 29 | 70 | 87 | 0 |
| 7 | $CHCl_2$ | $CH_2CH=CCl_2$ | $CH_2CH=CCl_2$ | — | — | — | 42* | 0 PRE |
| | | | | — | — | — | — | 21 |
| 8 | $CHCl_2$ | $CH_2CH=CHCl$ | $CH_2CH=CH_2$ | — | — | — | 83* | |
| | | | | 20 | 36 | 56 | 68 | 0 |
| 9 | $CF_3$ | $CH_2CH=CHCl$ | $CH_2CH=CHCl$ | 60 | 68 | 73 | 85 | 0 PRE |
| 10 | carboxyvinyl | $CH_2CH=CHCl$ | $CH_2CH=CHCl$ | — | — | — | $39^c$ | 0 |
| 11 | carboxy-(1 or 2-chlorovinyl) (isomeric mixture) | $CH_2CH=CHCl$ | $CH_2CH=CHCl$ | — | — | — | $31^c$ | 0 |
| 12 | carboxy-(1,2-dichlorovinyl) | $CH_2CH=CHCl$ | $CH_2CH=CHCl$ | — | — | — | $49^c$ | 3 |
| 13 | H | $CH_2CH=CHCl$ | $CH_2CH=CHCl$ | — | — | — | $28^c$ | 0 |
| 14 | $CH_3SCH_2$ | $CH_2CH=CHCl$ | $CH_2CH=CHCl$ | — | — | — | 68 | 0 |
| 15 | $CCl_3$ | $CH_2CH=CHCl$ | furfuryl | — | — | — | 99 | 0 |
| | | | | 43 | 60 | 80 | 99 | |
| 16 | $CCl_3$ | $CH_2CH=CHCl$ | methoxyethyl | — | — | — | 100 | 0 |
| | | | | 43 | 41 | 96 | 99 | |
| 17 | $CCl_3$ | $CH_2CH=CHCl$ | 2-methylallyl | — | — | — | 98 | 0 |
| | | | | 96 | 97 | 100 | 99 | |
| 18 | $CH_3CCl_2$ | $CH_2CH=CHCl$ | $CH_2CH=CHCl$ | — | — | — | 99 | 0 |
| | | | | 46 | 49 | 85 | 94 | |
| 19 | $CCl_3$ | $CH_2CH=CHCl$ | cyclopropylmethyl | — | — | — | 99 | 0 |

TABLE 1-continued

HERBICIDAL ACTIVITY AND EXTENDING ACTIVITY OF EXTENDERS $$R^1-\overset{O}{\underset{\|}{C}}-N\overset{R^2}{\underset{R^3}{\diagup}}$$

|    | R¹ | R² | R³ | 59 | 80 | 98 | 99 |   |
|----|----|----|----|----|----|----|----|----|
| 20 | CCl₃ | CH₂CH=CHCl | benzyl | — | — | — | 68 | 0 |
| 21 | BrCH₂CHBr | CH₂CH=CHCl | CH₂CH=CHCl | — | — | — | 18 | 0 |
| 22 | CH₃CHBrCHBr | CH₂CH=CHCl | CH₂CH=CHCl | — | — | — | 27 | 0 |
| 23 | 1,2-dibromo-2-phenylethyl | CH₂CH=CHCl | CH₂CH=CHCl | — | — | • | 21 | 0 |
| 24 | 1,2-dibromo-2-(4'-chlorophenyl)ethyl | CH₂CH=CHCl | CH₂CH=CHCl | — | — | — | 18 | 0 |
| 25 | CCl₃ | CH₂CH=CHCl | 1,1-dimethylpropynyl | — | — | — | 30 | 4 |
| 26 | tert-butyl | CH₂CH=CHCl | CH₂CH=CHCl | — | — | — | 26 | 0 |
| 27 | 2,2-dimethylpropyl | CH₂CH=CHCl | CH₂CH=CHCl | — | — | — | 18 | 0 |
| 28 | 2,2-dimethyl-1-bromopropyl | CH₂CH=CHCl | CH₂CH=CHCl | — | — | — | 14 | 0 |
| 29 | isopropyl | CH₂CH=CHCl | CH₂CH=CHCl | — | — | — | 10 | 0 |
| 30 | 1,1-dimethyl-2-chloroethyl | CH₂CH=CHCl | CH₂CH=CHCl | — | — | — | 32 | 0 |
| 31 | CBr₃ | CH₂CH=CHCl | CH₂CH=CHCl | — | — | — | 54 | 0 |
| 32 | 4-chlorophenyl | CH₂CH=CHCl | CH₂CH=CHCl | — | — | — | 21 | 0 PRE |
| 33 | vinyl | CH₂CH=CHCl | CH₂CH=CHCl | — | — | — | 13 | 0 PRE |
| 34 | acetomethyl | CH₂CH=CHCl | CH₂CH=CHCl | — | — | — | 27 | 0 |
| 35 | methylsulfonylmethyl | CH₂CH=CHCl | CH₂CH=CHCl | — | — | — | 25 | 0 |
| 36 | 1-bromo-n-propyl | CH₂CH=CHCl | CH₂CH=CHCl | — | — | — | 46 | 0 |
| 37 | chloro-difluoromethyl | CH₂CH=CHCl | CH₂CH=CHCl | — | — | — | 48 | 0 |

**high cis and high trans are terms referring to batches of compounds containing a high proportion of 3-chloroallyl substituents at R¹ and R² in the cis- or trans- configuration, respectively.

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock. Preferred grinding aids are attapulgite clay, diatomaceous silica, synthetic fine silica and synthetic calcium and magnesium silicates.

Most preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anti-caking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with macroscopic dimensions. A typical particle is about 1 to 2 millimeters in diameter. Surfactants are often present to aid in leaching of the active ingredient from the granule or pellet.

The carrier is of mineral or organic origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salt, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular composition of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. INJECTION WITH ANHYDROUS AMMONIA

The herbicidal compositions of the instant invention comprising a thiolcarbamate herbicide and an amide extender and optionally an antidote can be applied to the soil by in-line injection with anhydrous ammonia. For pre-emergence soil injection applications of anhydrous ammonia, on conservation or conventional tilled acreage, the herbicidal composition of the instant invention can be introduced into the anhydrous line using a metering pump which offers a constant rate of the output per acre independent of the anhydrous ammonia output rate. The herbicidal composition discharge hose can tee into the ammonia discharge line between the meter and the manifold. Injection depth can be from 4 to 5 inches. The herbicidal compositions can also be injected with anhydrous ammonia in no-till situations.

Other herbicide products can be surface applied and incorporated at the same time the herbicidal compositions of the instant invention and anhydrous ammonia are injected, or post-emergent applications can be used.

F. IN GENERAL

Each of the above formulations can be prepared as a package containing both the herbicide and the extender together with the other ingredients of the formulation (diluents, emulsifiers, surfactants, etc.). The formulations can also be prepared by a tank mix method, in which the ingredients are obtained separately and combined at the grower site. The herbicide and extender may both be used in the same type of formulation or a different formulation may be used for each, e.g. the herbicide may be in microcapsule form while the extender may be an emulsifiable concentrate, or vice versa.

As a further alternative, the herbicide and extender can be applied sequentially, with either being applied first. This is a less preferred method, however, since more effective are obtained with simultaneous application.

In general, any conventional method of application can be used. The locus of application can be soil, seeds, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide/extender compositions and optionally an antidote can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide/extender composition and optional antidote in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. An herbicidal composition consisting essentially of
(1) an herbicidally effective amount of a thiolcarbamate having the formula $$R^4-S-\overset{\overset{O}{\|}}{C}-N\overset{R^5}{\underset{R^6}{}}$$

wherein
$R^4$ is $C_1$–$C_6$ alkyl;
$R^5$ and $R^6$ are $C_1$–$C_6$ alkyl
(2) an extending amount of a compound having the formula $$R^1-\overset{\overset{O}{\|}}{C}-N\overset{R^2}{\underset{R^3}{}}$$

wherein
$R^1$ is $C_1$–$C_6$ mono-, di-, tri- or polyhaloalkyl,
$R^2$ is mono- or di-haloallyl; and
$R^3$ is allyl, mono- or di-haloallyl, and
(3) a non-phytotoxic antidotally effective amount of a compound having the formula $$Cl_2CHC\overset{\overset{O}{\|}}{\phantom{C}}N\overset{CH_2-CH=CH_2}{\underset{CH_2-CH=CH_2}{}} \qquad (a)$$

2. A method of controlling undesirable vegetation comprising applying to the locus where control is desired
(1) an herbicidally effective amount of a thiolcarbamate herbicide having the formula $$R^4-S-\overset{\overset{O}{\|}}{C}-N\overset{R^5}{\underset{R^6}{}}$$

wherein
$R^4$ is $C_1$–$C_6$ alkyl;
$R^5$ and $R^6$ are $C_1$–$C_6$ alkyl
(2) an extending amount of a compound having the formula $$R^1-\overset{\overset{O}{\|}}{C}-N\overset{R^2}{\underset{R^3}{}}$$

wherein
$R^1$ is $C_1$–$C_6$ mono-, di-, tri- or poly-haloalkyl;
$R^2$ is mono- or di-haloallyl; and
$R^3$ is allyl, mono- or di-haloallyl,
(3) a non-phytotoxic antidotally effective amount of a thiolcarbamate herbicide antidote having the formula

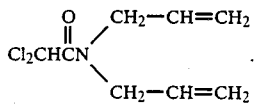

3. A method a non-phytotoxic antidotally effective amount of a compound having the formula of controlling undesirable vegetation, reducing herbicidal crop injury due to a thiolcarbamate herbicide, and minimizing the soil degradation thus extending the soil life of such a thiolcarbamate herbicide, which comprises applying to the locus where control is desired the following composition:
(1) an herbicidally effective amount of a thiolcarbamate having the formula

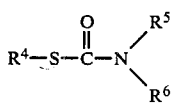

wherein
$R^4$ is $C_1$–$C_6$ alkyl
$R^5$ and $R^6$ are $C_1$–$C_6$ alkyl
(2) an amount of a compound having the formula

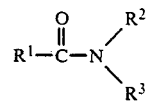

wherein
$R^1$ is $C_1$–$C_6$ mono-, di-, tri- or poly-haloalkyl,
$R^2$ is mono- or di-haloallyl; and
$R^3$ is allyl, mono- or di-haloallyl,
(3) a non-phytotoxic antidotally effective mount of an antidote having the formula

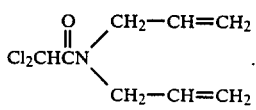

* * * * *

UNITED STATES PATENT AND TRADEMARK OFFICE
CERTIFICATE OF CORRECTION

PATENT NO. : 4,762,548

DATED : August 9, 1988

INVENTOR(S) : Reed A. Gray et al.

It is certified that error appears in the above-identified patent and that said Letters Patent is hereby corrected as shown below:

In Column 3, last line, ..."$C_4$-$C_8$ alkylene; and" should read "$C_4$-$C_9$ alkylene; and".

In Column 6, line 51, "washed with water and..." should read "washed twice with water and...".

In column 16, Table I, entry for Cmpd. No. 5 under column headed 3 + 2 which reads "9", should read "8".

In column 22, at line 37, after the formula, insert "wherein the weight ratio of herbicide to antidote is from about 0.1:1 to about 40:1."

In column 22, line 65, after "...or dihaloallyl," insert "and further".

In column 23, at line 7, after the formula, insert "wherein the weight ratio of herbicide to antidote is from about 0.1:1 to about 30:1.".

In column 24, between lines 14 and 15, after "$R^3$ is allyl, mono- or di-haloallyl," insert "the amount of said compound being sufficient to extend the soil life of said thiolcarbamate; and".

In column 24, line 25, after the formula, insert "wherein the weight ratio of herbicide to antidote is from about 0.1:1 to about 30:1.".

Signed and Sealed this

Fourteenth Day of February, 1989

Attest:

DONALD J. QUIGG

*Attesting Officer*   *Commissioner of Patents and Trademarks*